(12) United States Patent
Becker

(10) Patent No.: US 11,779,771 B2
(45) Date of Patent: Oct. 10, 2023

(54) IMPLANTABLE MEDICAL DEVICE FOR STIMULATING A HUMAN OR ANIMAL HEART EMPLOYING AN EVALUATION OF SIGNALS BETWEEN A HIS ELECTRODE AND A FURTHER ELECTRODE

(71) Applicant: BIOTRONIK SE & CO. KG, Berlin (DE)

(72) Inventor: Frank Becker, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 79 days.

(21) Appl. No.: 17/324,282

(22) Filed: May 19, 2021

(65) Prior Publication Data
US 2021/0361953 A1 Nov. 25, 2021

(30) Foreign Application Priority Data
May 19, 2020 (EP) ..................................... 20175429

(51) Int. Cl.
*A61N 1/37* (2006.01)
*A61N 1/365* (2006.01)

(52) U.S. Cl.
CPC ....... *A61N 1/3712* (2013.01); *A61N 1/36521* (2013.01); *A61N 1/3706* (2013.01)

(58) Field of Classification Search
None
See application file for complete search history.

(56) References Cited

U.S. PATENT DOCUMENTS

| | | | |
|---|---|---|---|
| 8,725,257 B2 | 5/2014 | Maskara et al. | |
| 8,942,805 B2 | 1/2015 | Shuros et al. | |
| 2005/0137671 A1 | 6/2005 | Liu et al. | |
| 2014/0172035 A1 | 6/2014 | Shuros et al. | |
| 2019/0022378 A1 | 1/2019 | Prillinger et al. | |
| 2019/0275329 A1 | 9/2019 | Brisben et al. | |
| 2020/0129772 A1 | 4/2020 | Casavant et al. | |

*Primary Examiner* — Catherine M Voorhees
*Assistant Examiner* — Elizabeth K So
(74) *Attorney, Agent, or Firm* — Laurence A. Greenberg; Werner H. Stemer; Ralph E. Locher

(57) ABSTRACT

An implantable medical device stimulates a human or animal heart. The medical device contains a processor, a memory unit, a His electrode having a first electrode pole configured to detect an electrical signal at a His bundle of a heart, and a further electrode having a further electrode pole configured to detect an electrical signal at a cardiac region of the same heart different from the His bundle. During operation of the device, performing the steps of: measuring electric signals at a His bundle of a heart with the first electrode pole; measuring electric signals at a cardiac region of the same heart different from the His bundle with the further electrode pole; and evaluating intracardiac electrogram signals and/or impedance signals measured between the first electrode pole and the further electrode pole, with the provision that this evaluating does not only contain a determination of an atrial-His bundle transition time.

11 Claims, 4 Drawing Sheets

IMPLANTABLE MEDICAL DEVICE FOR STIMULATING A HUMAN OR ANIMAL HEART EMPLOYING AN EVALUATION OF SIGNALS BETWEEN A HIS ELECTRODE AND A FURTHER ELECTRODE

CROSS-REFERENCE TO RELATED APPLICATION

This application claims the priority, under 35 U.S.C. § 119, of European patent application EP 20175429.8, filed May 19, 2020; the prior application is herewith incorporated by reference in its entirety.

BACKGROUND OF THE INVENTION

Field of the Invention

The present invention relates to an implantable medical device for stimulating a human or animal heart according to the preamble of the independent medical device claim, to a method for determining the condition of human or animal heart with such an implantable medical device according to the preamble of the independent method claim, and to a computer program product according to the preamble of the independent computer program product claim.

Implantable medical devices for stimulating a human or animal heart, such as pacemakers, have been known for a long time. They can perform different functions. Different stimulation programs can be carried out by an appropriate pacemaker to restore the treated heart to a normal state. Pacemakers are also known to stimulate the His bundle.

The His bundle is a bundle of specific heart muscle cells that is part of the cardiac conduction system. The His bundle is located distally of the atrioventricular node towards the apex of the heart.

There exist specific devices adapted for His bundle pacing, wherein a detecting (sensing) and stimulation electrode is not implanted into the ventricle of the human or animal heart be treated, but rather at or near to the His bundle of the heart. Such use of a His bundle electrode enables a particularly physiologic stimulation of the human or animal heart. It is possible to detect an intrinsic stimulation of the right ventricle (RV) of the human or animal heart at the His bundle, although the R wave signals are much smaller at the His bundle than in the right ventricle. Furthermore, stimulation signals of the His bundle itself are additionally detected with a His electrode.

U.S. Pat. No. 8,942,805 B2 describes the possibility of determining an intrinsic atrial-His bundle (AH) delay interval by an action potential mapping procedure.

BRIEF SUMMARY OF THE INVENTION

It is an object of the present invention to provide an implantable medical device for stimulating a human or animal heart that makes use of improved algorithms/functions with respect to existing algorithms/functions that are based on signals derived from a single electrode.

This object is achieved with an implantable medical device for stimulating a human or animal heart having the features of the independent medical device claim. Such an implantable medical device comprises a processor, a memory unit, a His electrode and at least one further electrode. The His electrode comprises a first electrode pole configured to detect an electrical signal at a His bundle of a human or animal heart. The at least one further electrode comprises at least one further electrode pole configured to detect an electrical signal at a cardiac region of the same heart. In this context, this cardiac region is different from the His bundle. Thus, in intended operation of the implantable medical device, the His electrode and the at least one further electrode contact different cardiac regions of one and the same heart.

It is possible that the implantable medical device comprises exactly one further electrode, wherein this one further electrode might comprise a single further electrode pole or two or more further electrode poles. Furthermore, it is also possible that the implantable medical device comprises more than one further electrode, wherein each of the further electrodes comprises a single further electrode pole or two or more further electrode poles. In case of a plurality (two or more) further electrodes, some of them might comprise a single further electrode pole, wherein others might comprise a plurality of further electrode poles.

According to the presently claimed invention, the memory unit comprises a computer-readable program that causes the processor to perform the steps explained in the following when executed on the processor.

First, electric signals at a His bundle of a human or animal heart are measured with the first electrode pole.

At the same time or with a temporal offset, electric signals at a cardiac region of the same heart different from the His bundle are measured with the at least one further electrode pole. Consequently, electric signals are measured at least two different cardiac regions of one and the same heart.

Afterwards, signals of an intracardiac electrogram (IEGM) and/or impedance signals are evaluated. Thereby, these IEGM signals and/or impedance signals are measured between the first electrode pole and the at least one further electrode pole. In this context, it is necessary that this evaluating does not only comprise a determination of an atrial-His bundle (AH) transition time (also denoted as AH delay interval). This is due to the fact that a knowledge of such atrial-His bundle transition time will not enable the implantable medical device to sufficiently improve algorithms or functions for stimulating a cardiac region of the heart.

An evaluation of signals detected between the His electrode and the at least one further electrode located at a cardiac region different from the His bundle of the same heart enables a wealth of improvements of existing algorithms/functions by considering additional physiologic data not measured or not considered in prior art implantable medical devices. Many implantable medical devices for stimulating the human or animal heart known from prior art only use signals derived from a single electrode such as a right ventricular electrode. However, such unipolar measurements of electrical signals are interference-prone. Therefore, in some instances also electric signals from other electrodes such as a right atrial electrode or a left ventricular electrode are used together with right ventricular signals according to prior art techniques. However, so far, general usage of His electrode signals has not been described. Surprisingly, it could be found that also use of electrical signals obtained with a His electrode can well be used for improving a diagnostic or a therapeutic method applied by an implantable medical device for stimulating the human or animal heart, even though signals of His bundle activity are generally much smaller than atrial or ventricular signals and are thus much more difficult to sense and to evaluate in a reliable manner.

In an embodiment, the implantable medical device is a pacemaker such as an implantable pulse generator (IPG). In an embodiment, the implantable medical device is an implantable cardioverter/defibrillator (ICD). In an embodiment, the implantable medical device is specifically adapted to deliver His bundle pacing to the heart to be stimulated.

In an embodiment, the cardiac region different from the His bundle is a right atrium, a right ventricle, or a left ventricle of the same heart. Thus, it is generally possible to measure and evaluate signals detected with the His electrode and a right atrial electrode, with the His electrode and a right ventricular electrode, and/or with the His electrode and a left ventricular electrode. In an embodiment, the at least one further electrode is a right ventricle electrode. In a further embodiment, the at least one further electrode is a left ventricular electrode.

In an embodiment, the computer-readable program causes the processor to determine the relation (in particular a ratio) between a signal detected by the first electrode and a signal detected by the at least one further electrode. By such relation, a particularly direct correlation between a His bundle signal and a signal derived from another cardiac region can be obtained. In doing so, a direct influence or interdependence between two signals of different cardiac regions (one of the cardiac regions being the His bundle of the heart) can be observed.

In an embodiment, the relation is or comprises a time relation between two signals. E.g., the relation can be a delay time between a cardiac excitation of different cardiac regions belonging to the same heart cycle so that conclusions can be drawn with respect to signal conduction in the heart.

In an embodiment, the relation is or comprises an amplitude relation between two signals. E.g., a different signal strength of a cardiac excitation of different cardiac regions belonging to the same heart cycle can allow to draw conclusions on the condition of the heart, e.g., the contractility of different cardiac regions.

In an embodiment, the computer-readable program causes the processor to determine the condition of the human or animal heart on the basis of the evaluated intracardiac electrogram signals and/or the evaluated impedance signals. Such a condition can be expressed in relative values and can be stored by the implantable medical device or transferred by the device to an evaluation unit. Then, medical staff can use this information as original data for drawing medically relevant conclusions like making a diagnosis. In an embodiment, the condition of the heart is a hemodynamic condition. In an embodiment, the condition of the heart is a contractility condition.

In an embodiment, the computer-readable program causes the processor to determine, based on the performed evaluating step, at least one parameter representative for a hemodynamics and/or a contractility of the heart. Once again, this parameter can be stored in the implantable medical device to be read out at a later stage or can be transferred by the medical device to a (remotely located) evaluation unit to immediately inform medical staff on the hemodynamic parameter or the contractility parameter of the evaluated heart.

In an embodiment, the computer-readable program causes the processor to adjust, based on the performed evaluating step, an algorithm for controlling the implantable medical device. In particular the determined condition of the heart and/or the determined parameter regarding the hemodynamics and/or the contractility of the heart are used to optimize stimulation and/or analysis parameters or algorithms of the implantable medical device. To give an example, a capture verification with respect to the His bundle electrode or a timing optimization of intended stimulation pulses can be the parameters to be optimized on the basis of the determined cardiac condition.

In an embodiment, the algorithm to be adjusted is chosen from the group consisting of a capture classification algorithm, an automatic threshold test (ATT), a beat-to-beat capture control algorithm, and a closed-loop stimulation (CLS) algorithm.

The capture classification algorithm is used to determine the type of His bundle capture by the His bundle electrode (first electrode). If exclusively the His bundle is captured by the His bundle electrode, a so-called selective capture is given. This results in a specific excitation of the right ventricle in a narrow time window after stimulating the His bundle. If not only the His bundle, but also surrounding myocardium is captured by the His bundle electrode, a so-called non-selective capture is given. This results in a less selective excitation of the right ventricle and ventricular contractions over a broader time window after a stimulus with the His electrode. Finally, if neither the His bundle nor the surrounding myocardium has been captured by the His electrode, a no capture situation is given.

The ATT algorithm is an already established algorithm that typically measures once a day the detection threshold of a cardiac region to be stimulated. Based on this ATT algorithm, the stimulation amplitude is adjusted as needed. If signals detected with the first electrode at the His bundle are additionally used for employing the ATT algorithm, the determined detection threshold or the efficacy of the new stimulation parameter can be double-checked or complemented with the help of the detected His electrode signals.

The beat-to-beat capture control algorithm is also an established algorithm that checks the efficacy of each right ventricle stimulation. For this purpose, once a day the right ventricular detection threshold is measured and optionally the stimulation amplitude is adjusted. This algorithm can be complemented by the method steps described herein such that not only an intracardiac electrogram based on right ventricular signals, but also based on right ventricular and His bundle signals is used for the capture classification and the determination of the right ventricular detection threshold.

The currently applied closed-loop stimulation (CLS) algorithm physiologically regulates the heart rate during any form of physical and mental stress in synchrony with metabolic needs. By also evaluating impedance signals measured between a right ventricular electrode and a His electrode, the condition of stress and the stimulation need can be even more accurately determined than in case of the currently used input information. This is due to the fact that the impedance signal of the unipolar right ventricular signals as well as the impedance of the bipolar right ventricular and His bundle signals change with changing contractility of the heart. The ratio of both changes can particularly well be used for improving the CLS algorithm.

In an embodiment, the at least one further electrode is a quadrupolar electrode having four electric poles. To give an example, the quadrupolar at least one further electrode can be a left ventricular electrode. In such a case, it is possible for each of the four electrode poles to pair with the His electrode. Thus, four different electrical signals between the His bundle and the left ventricle will be obtained. In doing so, it is, e.g., possible to detect changes of the effective length between two electrode poles (i.e., between the His electrode pole and each of the electrode poles of the quadrupolar electrode to determine the contractility of the heart. This information can be used as original data for subsequent diagnostic purposes and/or adjustments or optimizations of stimulation therapy to be applied by the implantable medical device.

In an embodiment, the computer-readable program causes the processor to determine a change of impedance between each of the four electric poles and the first electrode pole during a cardiac cycle over a first period of time. In this context, the first period of time is longer than a cardiac cycle, so that intercyclic variations of the impedance change can be determined. In an embodiment, the first period of time is a time between 1.5 seconds and 1 month, in particular between 5 seconds and 3 weeks, in particular between 10 seconds and 2 weeks, in particular between 30 seconds and 1 week, in particular between 1 minute and 6 days, in particular between 2 minutes and 5 days, in particular between 5 minutes and 4 days, in particular between 10 minutes and 3 days, in particular between 20 minutes and 2 days, in particular between 30 minutes and one day, in particular between 1 hour and 20 hours, in particular between 2 hours and 15 hours, in particular between 5 hours and 10 hours.

The impedance change is typically an indicator of a length change of the heart since the impedance of blood is smaller than the impedance of muscle tissue. Thus, the longer the conductivity pathway is established through blood, the lower is the impedance. The impedance and the dynamic of impedance change (after intrinsic or stimulated depolarization) are also an indicator of physical or mental stress of a patient. If a patient is under stress, the conductivity pathway of electrical signals in the heart is guided over a higher portion of muscle tissue than in case of a relaxed condition of the patient. Thus, the dynamic of impedance in case of stress is different from the impedance change in case of a relaxed condition. This is due to the fact that the heart muscle is more contracted in a stressed state than in a relaxed state. Thus, the electrode tip typically comprising the electrode pole is surrounded in a stressed state to a higher extent by muscle tissue than in a relaxed state.

In an aspect, the present invention relates to a method for determining the condition of a human or animal heart by an implantable medical device for stimulating a human or animal heart.

Such an implantable medical device comprises a processor, a memory unit, a His electrode and at least one further electrode. The His electrode comprises a first electrode pole configured to detect an electrical signal at a His bundle of a human or animal heart. The at least one further electrode comprises at least one further electrode pole configured to detect an electrical signal at a cardiac region of the same heart. In this context, this cardiac region is different from the His bundle. Thus, when carrying out the method, the His electrode and the at least one further electrode contact different cardiac regions of one and the same heart.

For carrying out the method, electric signals at a His bundle of a human or animal heart are measured with the first electrode pole.

At the same time or with a temporal offset, electric signals at a cardiac region of the same heart different from the His bundle are measured with the at least one further electrode pole. Consequently, electric signals are measured at least two different cardiac regions of one and the same heart.

Afterwards, signals of an intracardiac electrogram (IEGM) and/or impedance signals are evaluated. Thereby, these IEGM signals and/or impedance signals are measured between the first electrode pole and the at least one further electrode pole. In this context, it is necessary that this evaluating does not only comprise a determination of an atrial-His bundle (AH) transition time (also denoted as AH delay interval).

Finally, a condition of the heart is determined on the basis of the preceding evaluating step. In this context, it should be noted that this determining does not encompass a diagnostic step. Rather, the determined condition serves as original data on the basis of which a diagnosis can be made later on by medical staff considering further factors, data and/or information.

In an aspect, the present invention relates to a diagnostic method comprising all method steps of the precedingly explained method, but additionally also comprises a step of making a diagnosis with respect to a specific health condition or disease condition of the patient, the heart of whom has been examined. This diagnosis can, in an embodiment, be automatically be performed by the implantable medical device. In an embodiment, the result of the diagnosis is stored within the implantable medical device or transferred to a display or an evaluation unit and is optionally displayed or presented on a (printed) report comprising further information on the patient and/or physiologic patient parameters.

In an aspect, the present invention relates to a computer program product comprising computer-readable code that causes the processor to perform the steps explained in the following when executed on the processor.

First, electric signals at a His bundle of a human or animal heart are measured with a His electrode having a first electrode pole.

At the same time or with a temporal offset, electric signals at a cardiac region of the same heart different from the His bundle are measured with at least one further electrode having at least one further electrode pole. Consequently, electric signals are measured at at least two different cardiac regions of one and the same heart.

Afterwards, signals of an intracardiac electrogram (IEGM) and/or impedance signals are evaluated. Thereby, these IEGM signals and/or impedance signals are measured between the first electrode pole and the at least one further electrode pole. In this context, it is necessary that this evaluating does not only comprise a determination of an atrial-His bundle (AH) transition time (also denoted as AH delay interval).

In an aspect, the present invention relates to a medical method of treatment of a human or animal patient in need of such treatment by means of an implantable medical device for stimulating a human or animal heart.

This method is carried out with the help of an implantable medical device for stimulating a human or animal heart. Such an implantable medical device comprises a processor, a memory unit, a His electrode and at least one further electrode. The His electrode comprises a first electrode pole configured to detect an electrical signal at a His bundle of a human or animal heart. The at least one further electrode comprises at least one further electrode pole configured to detect an electrical signal at a cardiac region of the same heart. In this context, this cardiac region is different from the His bundle. Thus, when carrying out the method, the His electrode and the at least one further electrode contact different cardiac regions of one and the same heart.

First, electric signals at a His bundle of a human or animal heart are measured with a His electrode having a first electrode pole.

At the same time or with a temporal offset, electric signals at a cardiac region of the same heart different from the His bundle are measured with at least one further electrode having at least one further electrode pole.

Consequently, electric signals are measured at least two different cardiac regions of one and the same heart.

Afterwards, signals of an intracardiac electrogram (IEGM) and/or impedance signals are evaluated. Thereby, these IEGM signals and/or impedance signals are measured between the first electrode pole and the at least one further electrode pole. In this context, it is necessary that this evaluating does not only comprise a determination of an atrial-His bundle (AH) transition time (also denoted as AH delay interval).

Afterwards, an algorithm for controlling the implantable medical device is adjusted on the basis of the preceding evaluating step.

Finally, a cardiac region of the human or animal heart is stimulated with the His electrode, with the at least one further electrode and/or with a stimulation unit configured to stimulate a cardiac region of the heart. In this context, the stimulation is performed by applying the adjusted algorithm. Thus, the conclusions drawn from the evaluation of the His bundle signal in connection with the signal of at least a further cardiac region is used to adapt the stimulation of a cardiac region of the heart by applying an adjusted stimulation algorithm.

All embodiments of the implantable medical device can be combined in any desired way and can be transferred either individually or in any arbitrary combination to the described methods and the described computer program product. Likewise, all embodiments of the described methods can be combined in any desired way and can be transferred either individually or in any arbitrary combination to the respective other method, to the implantable medical device and to the computer program product. Finally, all embodiments described with respect to the computer program product can be combined in any desired way and can be transferred either individually or in any arbitrary combination to the described implantable medical device or to the described methods.

Other features which are considered as characteristic for the invention are set forth in the appended claims.

Although the invention is illustrated and described herein as embodied in an implantable medical device for stimulating a human or animal heart employing an evaluation of signals between a his electrode and a further electrode, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
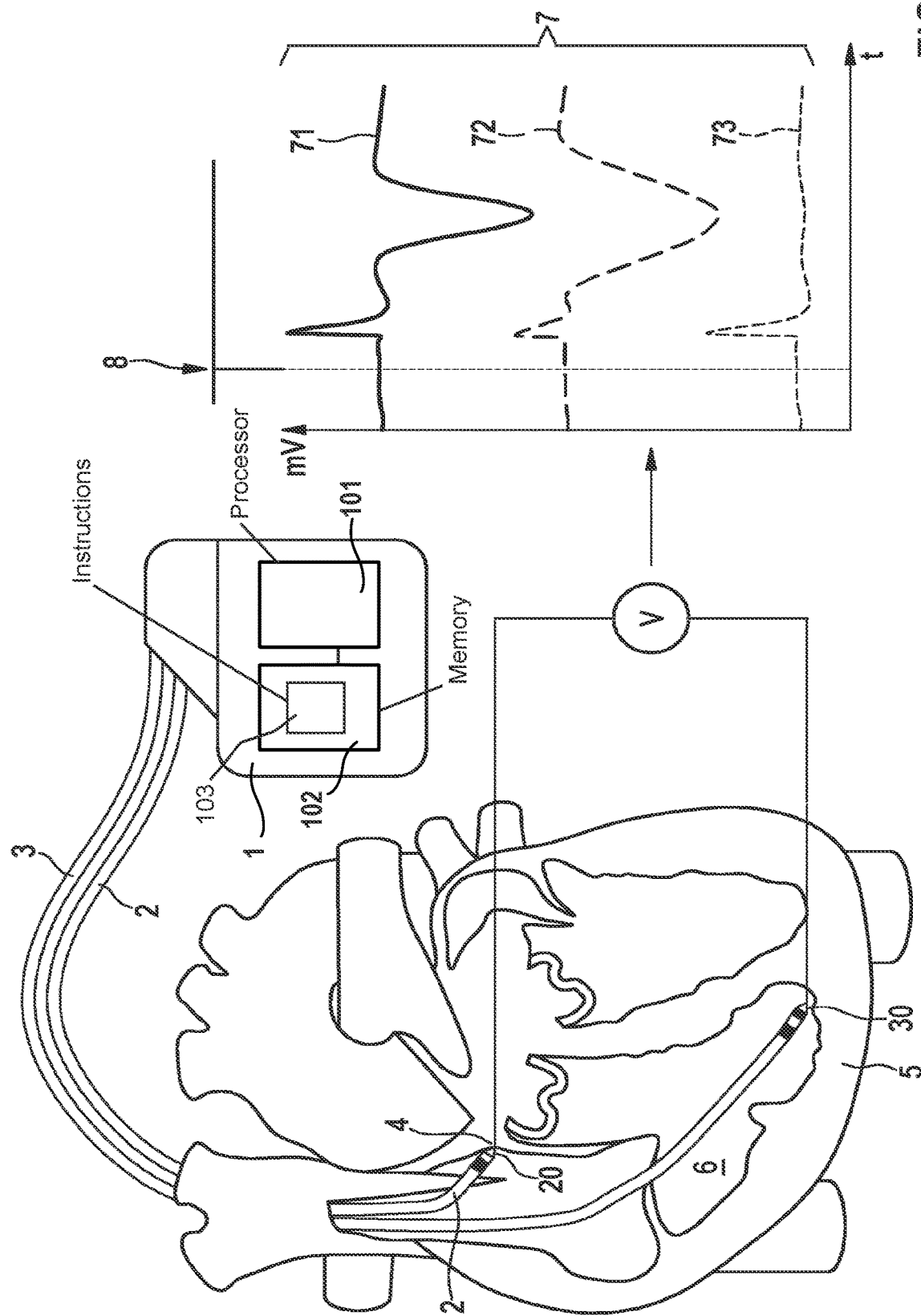
FIG. 1 is an illustration which schematically shows a first embodiment of an implantable medical device making use of data obtained by a His electrode and a right ventricular electrode along with schematic intracardiac electrograms.

Referring now to the figures of the drawings in detail and first, particularly to FIG. 1 thereof, there is shown an implantable pulse generator 1 as example for a device for stimulating the human heart. The implantable pulse generator 1 comprises a His electrode 2 and a right ventricular electrode 3. The His electrode 2 is implanted such as to contact a His bundle 4 of a human heart 5, wherein the right ventricular electrode 3 is implanted such to contact the myocardium within a right ventricle 6 of the same heart 5.

During operation of the implantable pulse generator 1, and intracardiac electrogram (IEGM) between the His electrode 2 and the right ventricular electrode 3 is measured. On the right-hand side of FIG. 1, exemplary IEGMs 7 are depicted. Upon a stimulation pulse 8 with the His electrode 2, different types of IEGMs 7 can be detected. This depends on the exact positioning of the His electrode 2. In case of a selective capture of the His bundle 4, a elective capture IEGM 71 can be recorded. In case of a non-selective capture of the His bundle 4, a non-selective capture IEGM 72 can be recorded. In case that the His bundle is not captured at all, a no-capture IEGM 73 can be detected.

Thus, the different IEGMs 7 recorded between the His electrode 2 and the right ventricular electrode 3, or, to be more precise between a His electrode pole 20 serving as first electrode pole and a right ventricular electrode pole 30 serving as further electrode pole serve in assisting capture classification of the His bundle electrode 2. The information obtained by the IEGMs 7 recorded between the His electrode pole 20 and the right ventricular electrode pole 30 represents more exact and more reliable data than data obtained by relying only on a single electrode.

Figure 2:
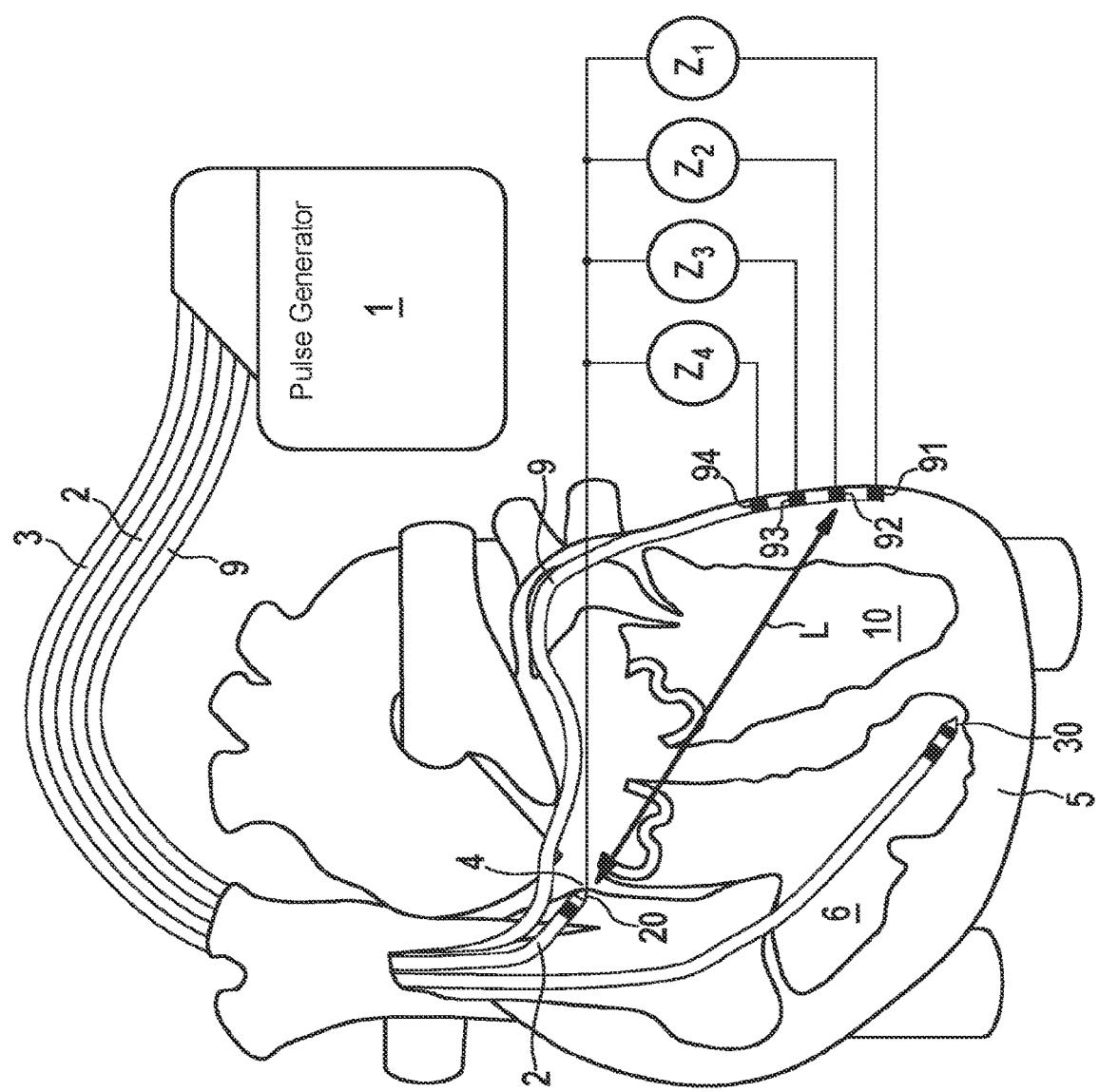
FIG. 2 is an illustration showing a second embodiment of an implantable medical device making use of data obtained by a His electrode and a left ventricular electrode.

FIG. 2 shows another embodiment of an implantable pulse generator 1, wherein similar elements are denoted with the same numeral references as in FIG. 1. The implantable pulse generator 1 of FIG. 2 also comprises a His electrode 2 and right ventricular electrode 3, but additionally also comprises a left ventricular electrode 9. As in case of the embodiment depicted in FIG. 1, the His electrode 2 comprises a His electrode pole 20 being in contact with a His bundle 4 of the human heart 5. Likewise, the right ventricular electrode 3 comprises a right ventricular electrode pole 30 contacting the myocardium within the right ventricle 6 of the same heart 5. The left ventricular electrode 9 comprises four electrode poles 91, 92, 93 and 94 that are in contact with myocardium at the left ventricle 10 of the same heart 5.

It is possible to measure a first impedance Z1 between the first left ventricular electrode pole 91 and the His electrode pole 20, a second impedance Z2 between the second left ventricular electrode pole 92 and the His electrode pole 20, a third impedance Z3 between a third left ventricular electrode pole 93 and the His electrode pole 20, as well as a fourth impedance Z4 between the fourth left ventricular electrode pole 94 and the His electrode pole 20.

In doing so, four different impedances Z1, Z2, Z3, and Z4 are obtained that can be used to determine a length L between each of the left ventricular electrode poles 91, 92, 93, and 94 as well as the His electrode pole 20.

By evaluating a change of the four impedances Z1, Z2, Z3, and Z4 over time, detailed information with respect to the contractility of the heart 5 are obtained. Thus, an online measurement of the contractility of the human heart 5 is possible. Consequently, it is possible to online determine any changes of the condition of the human heart with respect to its contractility that can be indicative for a pathologic change of the cardiac power of the heart 5. This, in turn, may require an adjustment of pacing algorithms applied by the implantable pulse generator 1 when stimulating the heart 5. These algorithms are then adjusted on the basis of the determined change of the contractility of the heart 5.

Figure 3:
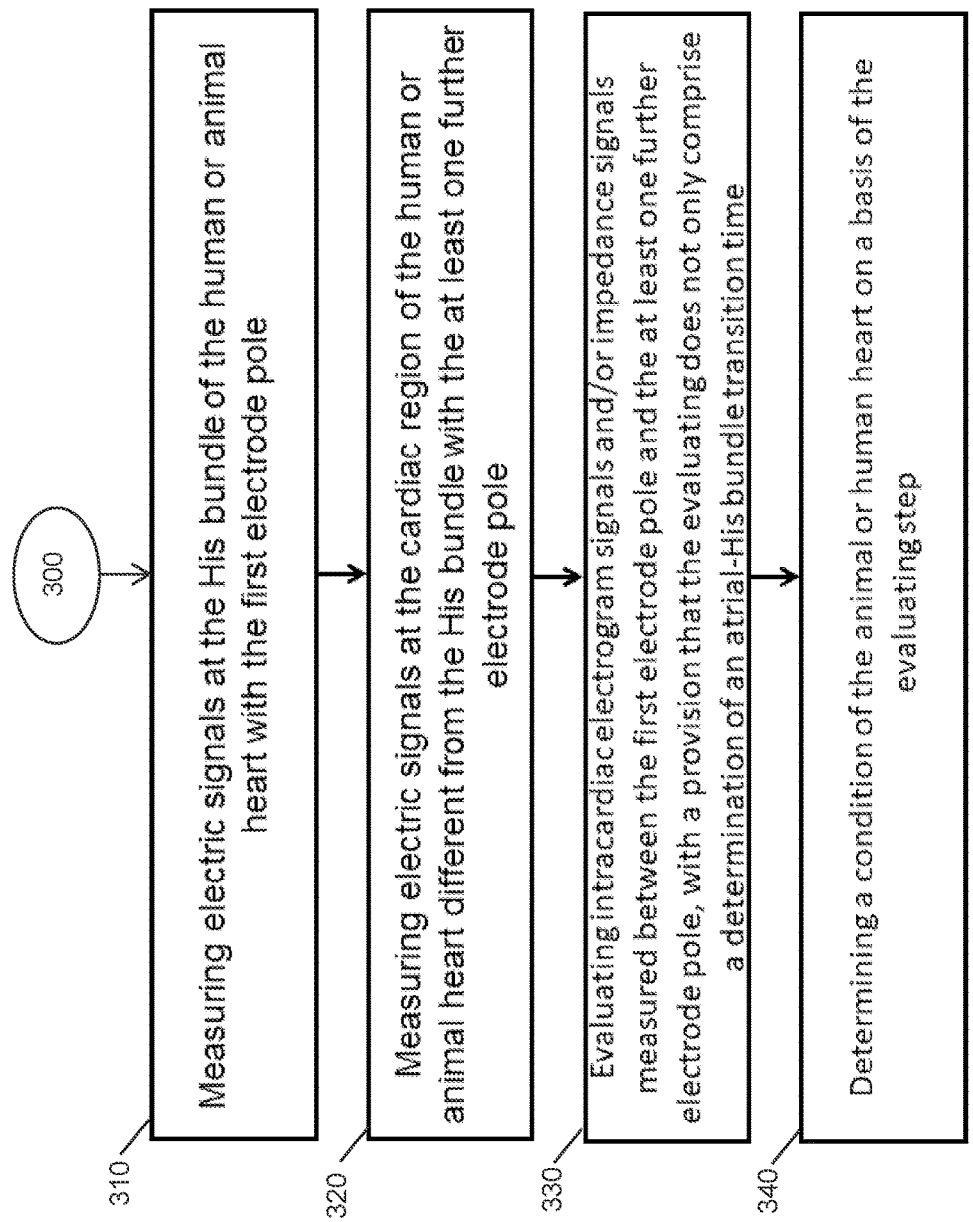
FIG. 3 is a diagram illustrating an exemplary embodiment of a method for determining a condition of a human or animal heart using an implantable medical device.

FIG. 3 is a diagram illustrating an exemplary embodiment of a method 300 for determining a condition of a human or animal heart using an implantable medical device, for example, an implantable pulse generator 1 for stimulating the human or animal heart. The implantable medical device has a processor 101 (shown in FIG. 1) and a memory unit 102 (shown in FIG. 1). As previously described regarding FIGS. 1 and 2, the implantable medical device also has a His electrode 2 having a first electrode pole 20 configured to detect an electrical signal at a His bundle 4 of the human or animal heart, and at least one further electrode having at least one further electrode pole configured to detect an electrical signal at a cardiac region of the human or animal heart different from the His bundle 4. The exemplary embodiment of the method 300 includes at least the steps described below. Step 310 includes measuring electric signals at the His bundle of the human or animal heart with the first electrode pole. Step 320 includes measuring electric signals at the cardiac region of the human or animal heart different from the His bundle with the at least one further electrode pole. Step 330 includes evaluating intracardiac electrogram signals and/or impedance signals measured between the first electrode pole and the at least one further electrode pole. Step 340 includes determining a condition of the animal or human heart on a basis of the evaluating step 330. The cardiac region different from the His bundle is a right atrium, a right ventricle or a left ventricle. Computer-readable instructions 103 (shown in FIG. 1) cause the processor 101 (shown in FIG. 1) to determine a relation between a signal detected by the first electrode pole and a signal detected by the at least one further electrode. The relation is or contains a time relation between the two signals.

Figure 4:
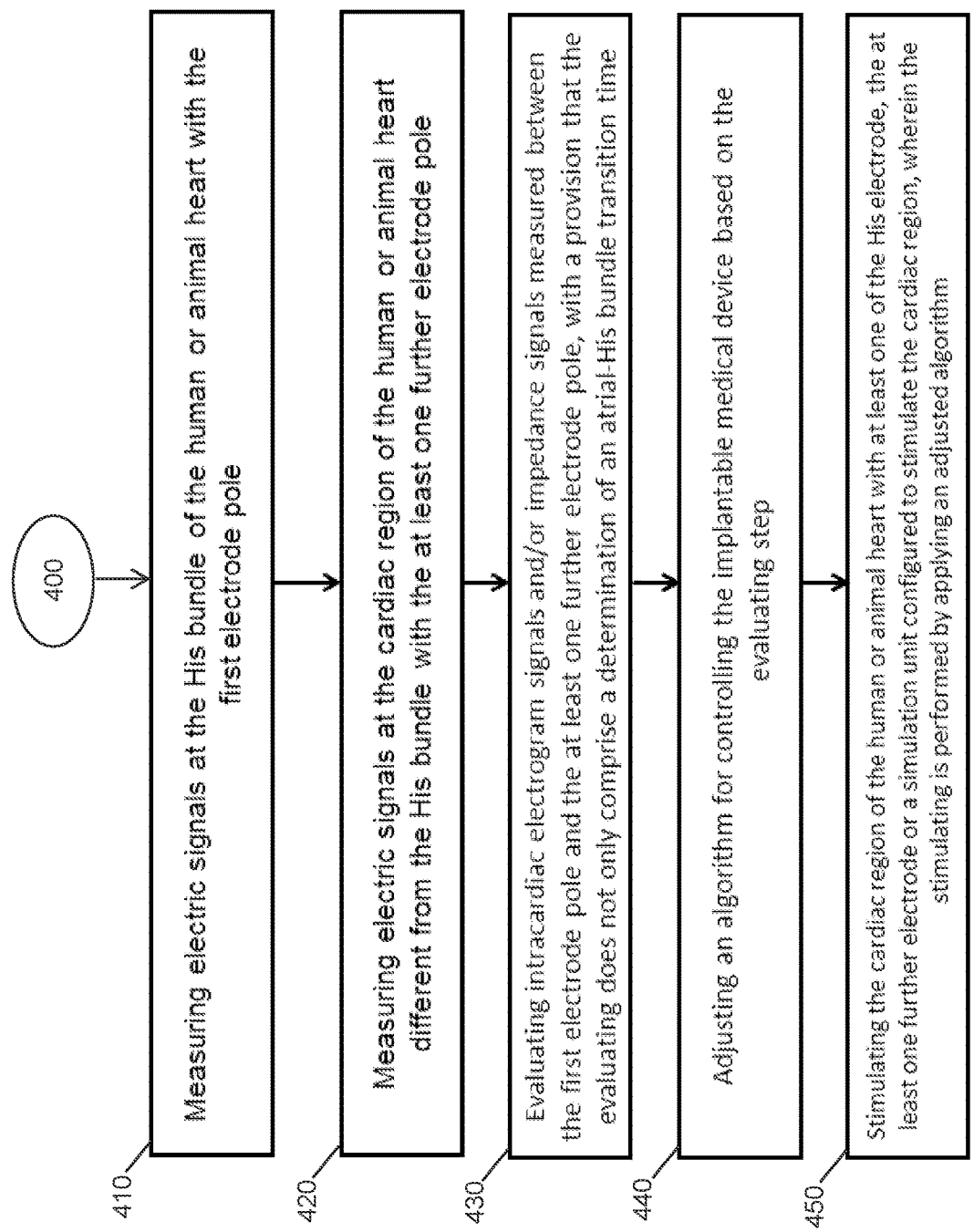
FIG. 4 is a diagram illustrating another exemplary embodiment of a method for determining a condition of a human or animal heart using an implantable medical device.

FIG. 4 is a diagram illustrating another exemplary embodiment of a method 400 of treatment of a human or animal patient by using an implantable medical device, for example, an implantable pulse generator 1 for stimulating the human or animal heart. The implantable medical device has a processor 101 (shown in FIG. 1) and a memory unit 102 (shown in FIG. 1). As previously described regarding FIGS. 1 and 2, the implantable medical device also has a His electrode 2 having a first electrode pole 20 configured to detect an electrical signal at a His bundle 4 of the human or animal heart, and at least one further electrode having at least one further electrode pole configured to detect an electrical signal at a cardiac region of the human or animal heart that is different from the His bundle 4. The exemplary embodiment of the method 400 includes at least the steps described below. Step 410 includes measuring electric signals at the His bundle of the human or animal heart with the first electrode pole. Step 420 includes measuring electric signals at the cardiac region of the human or animal heart different from the His bundle with the at least one further electrode pole. Step 430 includes evaluating intracardiac electrogram signals and/or impedance signals measured between the first electrode pole and the at least one further electrode pole. Step 440 includes adjusting an algorithm for controlling the implantable medical device based on the evaluating step. Step 450 includes stimulating the cardiac region of the human or animal heart with at least one of the His electrode, the at least one further electrode or a simulation unit configured to stimulate the cardiac region; the stimulating is performed by applying an adjusted algorithm. The cardiac region different from the His bundle is a right atrium, a right ventricle or a left ventricle. Computer-readable instructions 103 (shown in FIG. 1) cause the processor 101 (shown in FIG. 1) to determine a relation between a signal detected by the first electrode pole and a signal detected by the at least one further electrode. The relation is or contains a time relation between the two signals.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention claimed is:

1. An implantable medical device for stimulating a human or animal heart, the implantable medical device comprising:
   a processor;
   a His electrode having a first electrode pole configured to detect an electrical signal at a His bundle of the human or animal heart;
   at least one further electrode having at least one further electrode pole configured to detect an electrical signal at a cardiac region of the human or animal heart being different from the His bundle;
   a memory unit having computer-readable instructions causing said processor to perform the following steps when executed on said processor:
      measure electric signals at the His bundle of the human or animal heart with said first electrode pole;
      measure electric signals at the cardiac region of the human or animal heart being different from the His bundle with said at least one further electrode pole; and
      evaluate intracardiac electrogram signals and/or impedance signals measured between said first electrode pole and said at least one further electrode pole;
   wherein the cardiac region different from the His bundle is a right atrium, a right ventricle or a left ventricle;
   wherein the computer-readable instructions cause said processor to determine a relation between a signal detected by said first electrode pole and a signal detected by said at least one further electrode; and
   wherein the relation is or contains a time relation between the signal detected by said first electrode pole and the signal detected by said at least one further electrode.

2. The implantable medical device according to claim 1, wherein the relation is or comprises an amplitude relation between the two signals.

3. The implantable medical device according to claim 1, wherein the computer-readable instructions cause said processor to determine a condition of the human or animal heart on a basis of the intracardiac electrogram signals and/or the impedance signals.

4. The implantable medical device according to claim 1, wherein the computer-readable instructions cause said processor to determine, based on a performed evaluation, at least one parameter representative for a hemodynamics and/or a contractility of the human or animal heart.

5. The implantable medical device according to claim 1, wherein the computer-readable instructions cause said processor to adjust, based on a performed evaluation, an algorithm for controlling the implantable medical device.

6. The implantable medical device according to claim 5, wherein the algorithm is chosen from the group consisting of a capture classification algorithm, an automatic threshold test, a beat-to-beat capture control algorithm, and a closed loop stimulation algorithm.

7. The implantable medical device according to claim 1, wherein said at least one further electrode is a quadrupolar electrode having four electric poles.

8. The implantable medical device according to claim 7, wherein the computer-readable instructions cause said processor to determine a change of an impedance between each of said four electric poles and said first electric pole during a cardiac cycle over a first period of time.

9. A method for determining a condition of a human or animal heart using an implantable medical device for stimulating the human or animal heart, the implantable medical device having a processor, a memory unit, a His electrode having a first electrode pole configured to detect an electrical signal at a His bundle of the human or animal heart, at least one further electrode having at least one further electrode pole configured to detect an electrical signal at a cardiac region of the human or animal heart different from the His bundle, the method comprises the following steps of:
  measuring electric signals at the His bundle of the human or animal heart with the first electrode pole;
  measuring electric signals at the cardiac region of the human or animal heart different from the His bundle with the at least one further electrode pole;
  evaluating intracardiac electrogram signals and/or impedance signals measured between the first electrode pole and the at least one further electrode pole; and
  determining a condition of the animal or human heart on a basis of the evaluating step;
  wherein the cardiac region different from the His bundle is a right atrium, a right ventricle or a left ventricle;
  wherein computer-readable instructions cause the processor to determine a relation between a signal detected by the first electrode pole and a signal detected by the at least one further electrode; and
  wherein the relation is or contains a time relation between the signal detected by the first electrode pole and the signal detected by the at least one further electrode.

10. A non-transitory computer readable medium containing computer-readable code that causes a processor to perform the following steps when executed on the processor:
  measure electric signals at a His bundle of a human or animal heart with a His electrode having a first electrode pole;
  measure electric signals at a cardiac region of the human or animal heart different from the His bundle with at least one further electrode having at least one further electrode pole; and
  evaluate intracardiac electrogram signals and/or impedance signals measured between the first electrode pole and the at least one further electrode pole;
  wherein the cardiac region different from the His bundle is a right atrium, a right ventricle or a left ventricle;
  wherein computer-readable instructions cause the processor to determine a relation between a signal detected by the first electrode pole and a signal detected by the at least one further electrode; and
  wherein the relation is or contains a time relation between the signal detected by the first electrode pole and the signal detected by the at least one further electrode.

11. A method of treatment of a human or animal patient by means of an implantable medical device for stimulating the human or animal heart, wherein the implantable medical device containing a processor, a memory unit, a His electrode having a first electrode pole configured to detect an electrical signal at a His bundle of the human or animal heart, and at least one further electrode having at least one further electrode pole configured to detect an electrical signal at a cardiac region of the human or animal heart different from the His bundle, the method comprises the following steps of:
  measuring electric signals at the His bundle of the human or animal heart with the first electrode pole;
  measuring electric signals at the cardiac region of the human or animal heart different from the His bundle with the at least one further electrode pole;
  evaluating intracardiac electrogram signals and/or impedance signals measured between the first electrode pole and the at least one further electrode pole;
  adjusting an algorithm for controlling the implantable medical device based on the evaluating step; and
  stimulating the cardiac region of the human or animal heart with at least one of the His electrode, the at least one further electrode or a simulation unit configured to stimulate the cardiac region, wherein the stimulating is performed by applying an adjusted algorithm;
  wherein the cardiac region different from the His bundle is a right atrium, a right ventricle or a left ventricle;
  wherein computer-readable instructions cause the processor to determine a relation between a signal detected by the first electrode pole and a signal detected by the at least one further electrode; and
  wherein the relation is or contains a time relation between the signal detected by the first electrode pole and the signal detected by the at least one further electrode.

* * * * *